(12) United States Patent
Amano et al.

(10) Patent No.: US 9,823,180 B2
(45) Date of Patent: Nov. 21, 2017

(54) METHOD FOR MEASURING RESISTANCE OF CONVEYOR BELT TO GETTING OVER SUPPORT ROLLER, AND DEVICE THEREFOR

(71) Applicant: The Yokohama Rubber Co., LTD., Minato-ku, Tokyo (JP)

(72) Inventors: Shigehiko Amano, Hiratsuka (JP); Gang Hou, Hiratsuka (JP); Toru Fujii, Hiratsuka (JP); Kazuya Okubo, Hiratsuka (JP)

(73) Assignee: The Yokohama Rubber Co., LTD. (JP)

( * ) Notice: Subject to any disclaimer, the term of this patent is extended or adjusted under 35 U.S.C. 154(b) by 403 days.

(21) Appl. No.: 14/404,342

(22) PCT Filed: Jun. 12, 2013

(86) PCT No.: PCT/JP2013/066213
§ 371 (c)(1),
(2) Date: Nov. 26, 2014

(87) PCT Pub. No.: WO2013/187437
PCT Pub. Date: Dec. 19, 2013

(65) Prior Publication Data
US 2015/0241332 A1    Aug. 27, 2015

(30) Foreign Application Priority Data

Jun. 15, 2012   (JP) ................................. 2012-136182

(51) Int. Cl.
*G01N 19/02* (2006.01)
*G01N 3/08* (2006.01)

(52) U.S. Cl.
CPC ............... *G01N 19/02* (2013.01); *G01N 3/08* (2013.01)

(58) Field of Classification Search
CPC ...................................................... G01N 19/02
See application file for complete search history.

(56) References Cited

U.S. PATENT DOCUMENTS 4,762,005 A * 8/1988 Marshek ................. B24B 21/20
73/862.041
6,321,586 B1 * 11/2001 Wojtowicz ............... G01N 3/56
73/9

FOREIGN PATENT DOCUMENTS

JP    S62-265551     11/1987
JP    H03-061838     3/1991
(Continued)

OTHER PUBLICATIONS

International Search Report for International Application No. PCT/JP2013/066213 dated Jul. 23, 2013, 4 pages, Japan.

*Primary Examiner* — Robert R Raevis
(74) *Attorney, Agent, or Firm* — Thorpe North & Western

(57) ABSTRACT

An evaluation subject formed by a cut sample of a conveyor belt is mounted on a flat substrate with an inner periphery-side cover rubber layer located on the upper side, a support roller mounted in a frame is horizontally pulled and rolled in the longitudinal direction of the evaluation subject by pulling the frame by a wire while the support roller is pressed vertically downward against the upper surface of the evaluation subject at a preset pressure using a pneumatic cylinder without substantial deformation of the outer peripheral surface thereof, and tensile force in a horizontal direction measured at this time by a tensile force sensor connected to the wire is evaluated as resistance to moving over the support roller.

12 Claims, 5 Drawing Sheets

(56) References Cited

FOREIGN PATENT DOCUMENTS

| JP | 2002-082033 | 3/2002 |
| JP | 2005-156505 | 6/2005 |
| JP | 2006-292736 | 10/2006 |
| JP | 2008-275539 | 11/2008 |

* cited by examiner

METHOD FOR MEASURING RESISTANCE OF CONVEYOR BELT TO GETTING OVER SUPPORT ROLLER, AND DEVICE THEREFOR

TECHNICAL FIELD

The present technology relates to a method for measuring resistance of a conveyor belt to moving over a support roller, and to a device therefore. More specifically, the present technology relates to a method for measuring resistance of a conveyor belt to moving over a support roller capable of more simply and accurately measuring resistance to moving over the support roller while the conveyor belt is in operation, and to a device therefore.

BACKGROUND

It is known that power consumption for driving a conveyor belt changes according to the type of conveyor belt and peripheral equipment such as driving rollers, in addition to being influenced by changes or the like in the weight of transportation articles which are stacked on the conveyor belt. Since the number of support rollers which support the conveyor belt increases when the belt conveyor has a long length, power loss caused by contact between the conveyor belt and the support rollers is predominant in terms of the power consumption. Therefore, reducing the power loss occurring when moving over the support rollers, that is, the resistance to moving over the support rollers, has become an important issue.

When measuring the resistance to moving over support rollers using an actual belt conveyor device, it is necessary to have a large scale measuring device in addition to the actual conveyor belt. Therefore, a high cost is incurred and a long time is required for measurement and evaluation. Therefore, a method and a device for measuring the resistance to moving over a support roller using a cut sample of a conveyor belt as an evaluation subject, have been proposed (refer to Japanese Unexamined Patent Application Publication No. 2006-292736A).

In the technology proposed in Japanese Unexamined Patent Application Publication No. 2006-292736A, the actual conveyor belt is not necessary. In addition, it is possible to reduce the size of the device since the device has a structure so that the support roller is moved and rolled on the surface of the evaluation subject with the evaluation subject provided in a tensioned state and fixed. Therefore, it is possible to reduce the cost and time required for the measurement and evaluation. However, since a device which attaches a load cell to both ends of the evaluation subject and connects the load cell between the both ends in a tensioned state is necessary in this technology and a strain gauge is attached in the form of a cantilever to the rolling surface of the support roller, there is a problem in that the device is complicated. The support roller is given a special structure which is different to the original specifications so as to measure the degree of deformation, in the radial direction, of the outer peripheral surface of the support roller using the strain gauge. Therefore, it is also necessary to consider measurement errors caused by deformation of the outer peripheral surface of the support roller.

SUMMARY

The present technology provides a method for measuring resistance of a conveyor belt to moving over a support roller capable of more simply and accurately measuring resistance to moving over a support roller while the conveyor belt is in operation, and to a device therefore.

A method for measuring resistance of a conveyor belt to moving over a support roller of the present technology, in which the support roller is rolled in the longitudinal direction of an evaluation subject formed by a cut sample of the conveyor belt in a state where the support roller is pressed at a predetermined pressure against a surface of the evaluation subject, includes mounting the evaluation subject on a flat substrate, horizontally pulling and rolling the support roller in the longitudinal direction of the evaluation subject in a state where the support roller is pressed vertically downward at a preset pressure against an upper surface of the evaluation subject without substantial deformation of an outer peripheral surface of the support roller, and evaluating tensile force in the horizontal direction measured at that time as resistance to moving over the support roller.

A device for measuring resistance of a conveyor belt to moving over a support roller of the present technology, which has a support roller to be pressed at a predetermined pressure against a surface of an evaluation subject formed by a cut sample of the conveyor belt, and a rolling means for rolling the support roller in the longitudinal direction of the evaluation subject in the pressed state, includes a flat substrate for mounting the evaluation subject thereon, a pressing means for setting the support roller to a state of being pressed vertically downward at a preset pressure against an upper surface of the evaluation subject mounted on the substrate, a rolling means for horizontally pulling and rolling the support roller set to the pressed state in the longitudinal direction of the evaluation subject, and a tensile force sensor for measuring tensile force in the horizontal direction during the rolling, the support roller being configured so that an outer peripheral surface thereof is substantially not deformed in the pressed state.

According to the present technology, since the support roller is configured so that an outer peripheral surface of the support roller is substantially not deformed when the support roller is set to a state of being pressed vertically downward at a preset pressure against an upper surface of an evaluation subject mounted on a substrate, measuring errors caused by the deformation of the outer peripheral surface of the support roller do not occur. Therefore, there is an advantage in that the measurement accuracy is improved. Since the measuring device is constituted by the flat substrate, the pressing means, the rolling means, and the tensile force sensor, it is possible for the measuring device to be simple.

Here, for example, a cut sample of only an inner periphery-side cover rubber layer is used as the evaluation subject. In such a case, the manufacturing of the evaluation subject is easy. In addition, when the evaluation subject is provided in a tensioned state, accurate measurement is difficult since stretching occurs. However, since measuring is performed with the evaluation subject mounted onto a flat substrate without tension acting on the evaluation subject, accurate measurement is possible.

It is also possible to set the support roller to a state of being pressed vertically downward at the preset pressure against the upper surface of the evaluation subject using a pneumatic cylinder. In such a case, it is possible to prevent an excessive load being generated with respect to the measuring device and the evaluation subject.

By horizontally pulling and moving the support roller in the longitudinal direction of the evaluation subject in a state of non-contact with the evaluation subject, setting the tensile force in the horizontal direction measured at that time as the base tensile force, and setting the support roller to a state of being pressed at the preset pressure against the upper surface of the evaluation subject, it is also possible to evaluate a tensile force where the base tensile force is subtracted from the tensile force in the horizontal direction, which is measured when the support roller is horizontally pulled and rolled in the longitudinal direction of the evaluation subject, as the resistance to moving over the support roller. In such a case, when evaluating the resistance to moving over the support roller, it is possible to improve the measuring accuracy since various superfluous forces are excluded as the base tensile force.

It is also possible to interpose a plurality of low-friction sheets between the lower surface of the evaluation subject and the upper surface of the substrate. In such a case, it is possible to minimize adverse influence with respect to the measuring accuracy caused by friction between the evaluation subject and the substrate.

DETAILED DESCRIPTION

Figure 1:
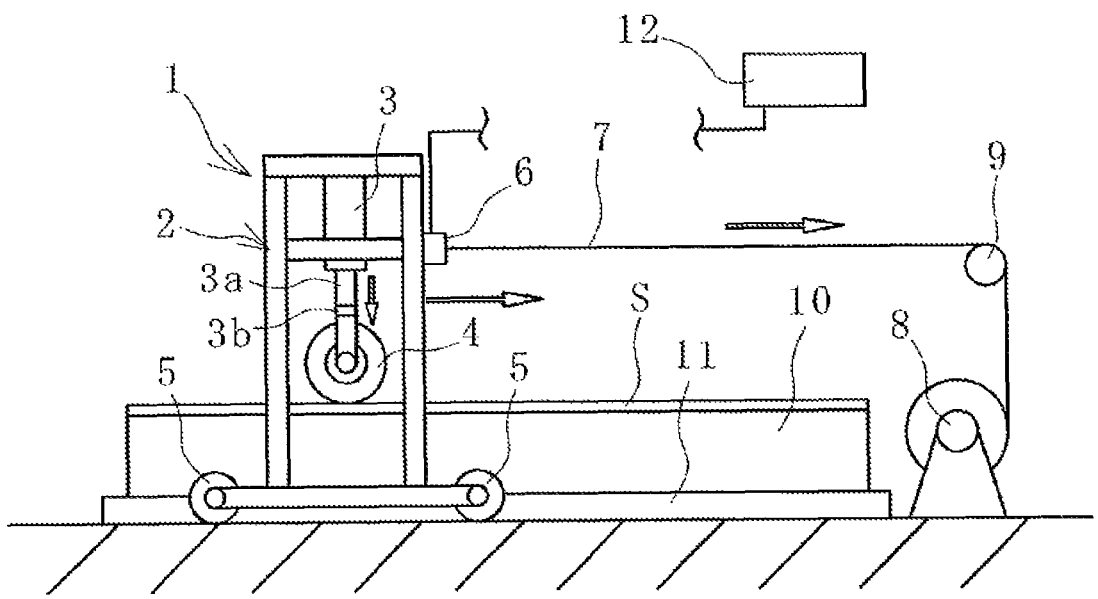
FIG. 1 is an explanatory drawing illustrating, as seen in side view, a device for measuring resistance to moving over a support roller of the present technology.

Below, description will be given of the method and device for measuring resistance to moving over a support roller of the present technology based on an embodiment illustrated in the drawings.

Figure 2:
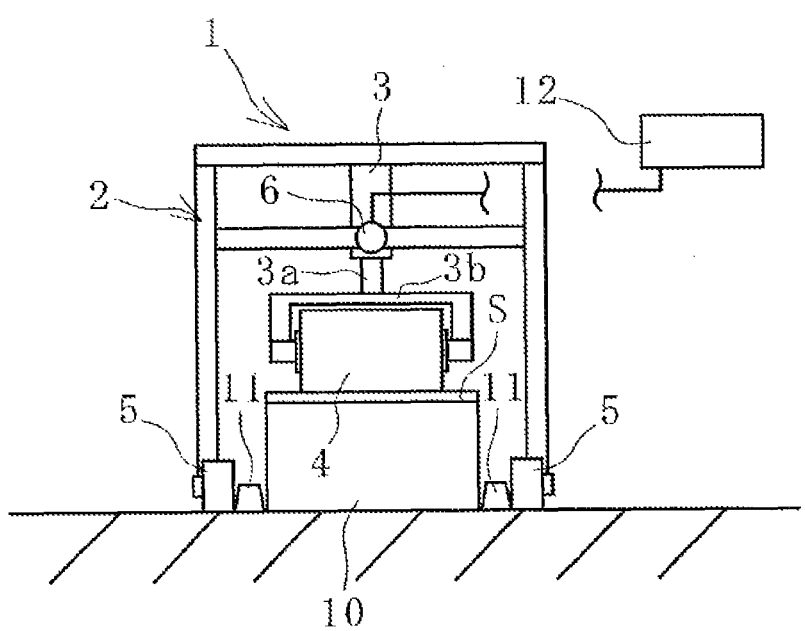
FIG. 2 is an explanatory drawing illustrating, as seen in front view, the measuring device in FIG. 1.
Figure 3:
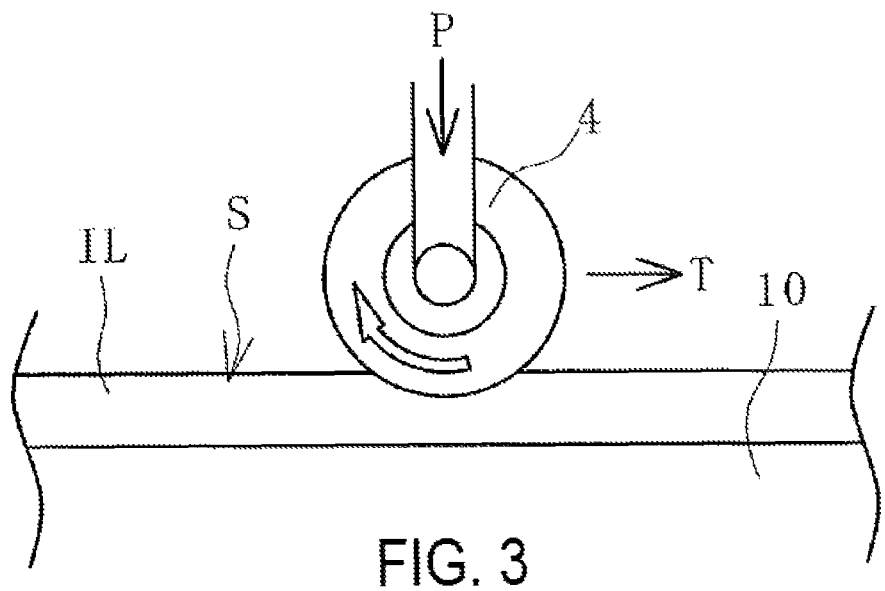
FIG. 3 is an enlarged view illustrating a periphery of the support roller in FIG. 1.

As illustrated in FIGS. 1 to 3, a device 1 for measuring resistance to moving over a support roller of the present technology (referred to below as the measuring device 1) is provided with a flat substrate 10 on which an evaluation subject S is mounted, a support roller 4, a pressing means which presses the support roller 4, a rolling means which rolls the support roller 4, and a tensile force sensor 6. The evaluation subject S is formed by a cut sample of a conveyor belt and is mounted on the substrate 10 with an inner periphery-side cover rubber layer IL set as the upper side. The inner periphery-side cover rubber layer IL is a cover rubber layer on the surface side which the support roller 4 comes into contact with and rolls on when the conveyor belt is installed by being wrapped around pulleys. On the other hand, the outer periphery-side cover rubber layer is a cover rubber layer on the surface side where the transportation articles are mounted. As long as the upper surface of the substrate 10 is smooth, for example, a table-shaped body made of metal such as stainless steel or steel may be used.

The support roller 4 is attached to a cylinder rod 3a of a pneumatic cylinder 3 installed vertically downward on a frame 2 arranged to straddle the substrate 10, so as to be able to move up and down via a holding frame 3b. Moving rollers 5 are provided on a lower end section of the frame 2, and the tensile force sensor 6 is installed on the front surface of the frame 2. For example, a load cell or the like may be used as the tensile force sensor 6, and a wire 7 which is wound by a winding machine 8 is connected thereto. The wire 7 is in a state of being horizontally provided in a tensioned state with the middle thereof being wound around a holding roller 9.

When the wire 7 is wound by the winding machine 8, the frame 2 is pulled in the horizontal direction and moved in the longitudinal direction of the evaluation subject S due to the rolling of the moving rollers 5. Here, moving guides 11 are provided to extend through between the moving rollers 5 on the left and right and the substrate 10 such that it is possible for the frame 2 (the moving rollers 5) to move straight forward without meandering.

The pressing means sets the support roller 4 to a state of being pressed vertically downward at a preset pressure P against the upper surface of the evaluation subject S mounted on the substrate 10. The pneumatic cylinder 3 is used as the pressing means in this embodiment. The rolling means horizontally pulls and rolls the support roller 4, which is set to the pressed state, in the longitudinal direction of the evaluation subject S. In this embodiment, the frame 2, which is provided with the moving rollers 5, the wire 7, and the winding machine 8 constitute the rolling means. The tensile force sensor 6 detects and measures a tensile force T in the horizontal direction of the support roller 4 rolling as described above. The measurement data is stored in a measuring apparatus 12.

The support roller 4 is configured to be substantially the same as a support roller 4a which is actually used in a conveyor belt CV described below. The peripheral surface of the support roller 4 is formed of a rigid body such as metal to have a sufficient thickness. Further, the support roller 4 is configured so that the outer peripheral surface thereof is substantially not deformed in the pressed state as described above.

Figure 6:
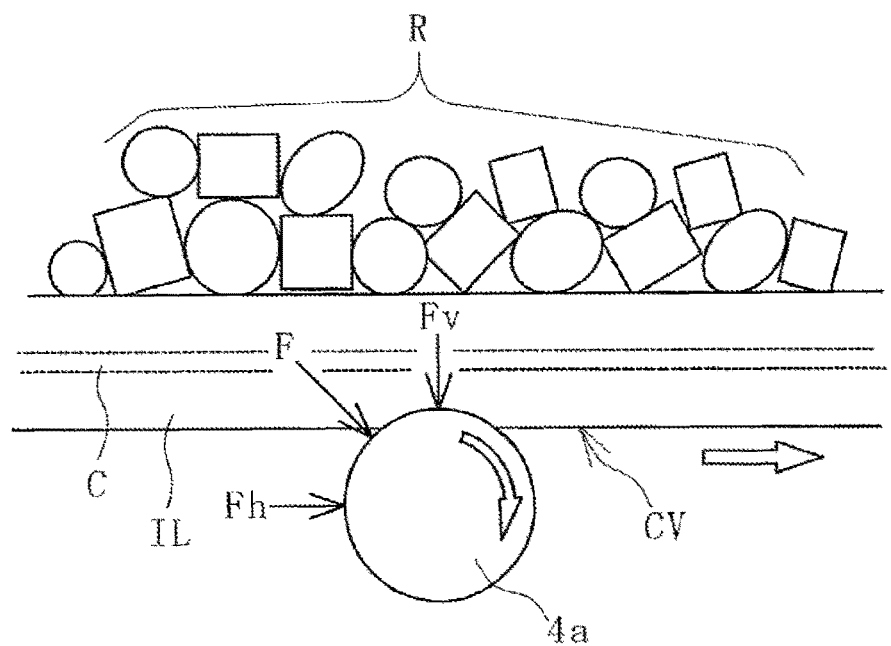
FIG. 6 is an explanatory drawing illustrating, as seen in side view, a conveyor belt which operates with transportation articles stacked thereon, and the support roller.

In the actual conveyor belt CV, transportation articles R are mounted and transported on the outer periphery-side cover rubber layer as illustrated in FIG. 6. The support roller 4a comes into contact with the inner periphery-side cover rubber layer IL of the conveyor belt CV and rolls. At this time, an external force F acts diagonally downward on the support roller 4a toward the belt traveling direction. Here, the energy loss W per unit of time which occurs when the conveyor belt CV gets over the support roller 4a is the external force F×belt velocity V. Since the support roller 4a is not displaced in the orthogonal direction, there is no loss due to the vertical component Fv of the external force F. Thus, when the horizontal component Fh of the external force F and the belt velocity V are determined, the energy loss per support roller 4a, that is, the belt moving over loss, is determined.

Therefore, the present technology has a configuration where the belt moving over loss per each support roller 4a is determined according to the horizontal component Fh in an aspect where the conveyor belt CV is fixed, and the support roller 4 is moved and rolled. That is, the evaluation subject S is mounted on the flat substrate 10 with the inner periphery-side cover rubber layer IL of the evaluation subject S set as the upper side, and the support roller 4 is set, without substantial deformation of the outer peripheral surface thereof, to a state of being pressed vertically downward at the preset pressure P against the upper surface of the evaluation subject S. In this state, the support roller 4 is horizontally pulled and rolled in the longitudinal direction of the evaluation subject S, and the tensile force T in the horizontal direction measured at that time is evaluated as the resistance to moving over the support roller.

Specifically, the cylinder rod 3a of the pneumatic cylinder 3 extends such that the support roller 4 is set to a state of being pressed at the preset pressure P against the upper surface of the evaluation subject S. Next, the support roller 4 is pulled and moved in the longitudinal direction of the evaluation subject S along with the frame 2 by operating the winding machine 8 to wind the wire 7. That is, the support roller 4 rolls in a state of being pressed at the pressure P against the evaluation subject S.

The tensile force T of the wire 7 at this time is successively detected and measured by the tensile force sensor 6, and the measurement data is stored in the measuring apparatus 12. The pressure P applied to the support roller 4 is set equivalent to the vertical component Fv which acts when the conveyor belt CV is used in practice. The movement velocity of the support roller 4 is set equivalent to the belt velocity when the conveyor belt CV is used in practice. Since the rolling velocity is not constant immediately after the start of the rolling of the support roller 4 and immediately before finishing of the rolling, the measurement data (the tensile force T) when the rolling velocity is constant may be evaluated as the resistance to moving over the support roller.

According to the present technology, as a result of having the support roller 4 configured so that the outer peripheral surface of the support roller 4, which is in a state of being pressed at the pressure P against the upper surface of the evaluation subject S mounted on the substrate 10, is substantially not deformed, measurement errors caused by the deformation of the outer peripheral surface of the support roller 4 do not occur in the measurement data of the tensile force T. Therefore, there is an advantage in that the measurement accuracy is improved. In addition, since the measuring device 1 is provided with the flat substrate 10, the pressing means, the rolling means, and the tensile force sensor 6, the constitution is simple. Since the measuring device 1 has a structure where the actual conveyor belt CV is not necessary and the support roller 4 is rolled on the surface of the evaluation subject S with the evaluation subject S set to a fixed state, it is easy to make the measuring device 1 more compact.

It is possible to use a cut sample where a core C is covered above and below by cover rubber layers or a cut sample of only the inner periphery-side cover rubber layer IL as the evaluation subject S. The size of the evaluation subject S is, for example, approximately 1500 mm to 5000 mm long and approximately 100 mm to 250 mm wide. When a cut sample of only the inner periphery-side cover rubber layer IL is used as the evaluation subject S, the manufacturing of the evaluation subject S is easy and it is possible to reduce the manufacturing time and costs. When the evaluation subject formed of only the inner periphery-side cover rubber layer IL is provided in a tensioned state, accurate measurement is difficult since stretching occurs. However, since measuring is performed with the evaluation subject S mounted onto the flat substrate 10 without tension acting on the evaluation subject S in the present technology, accurate measurement is possible. In addition, it is possible to ascertain the resistance to moving over the support roller purely for the inner periphery-side cover rubber layer IL.

When the pneumatic cylinder 3 is employed as the pressing means, even when the support roller 4 (the frame 2) is displaced up and down during the rolling of the support roller 4, the up and down displacement thereof is smoothly absorbed. Therefore, it is possible to prevent an excessive load being generated with respect to the measuring device 1 and the evaluation subject S.

As illustrated in FIG. 3, in a case where the tensile force T is measured by directly mounting the evaluation subject S on the substrate 10, friction may occur between the evaluation subject S and the substrate 10 due to the evaluation subject S being pulled by the rolling support roller 4, depending on the specifications of the evaluation subject S or the substrate 10. When such friction occurs, errors occur in the measured tensile force T.

Figure 4:
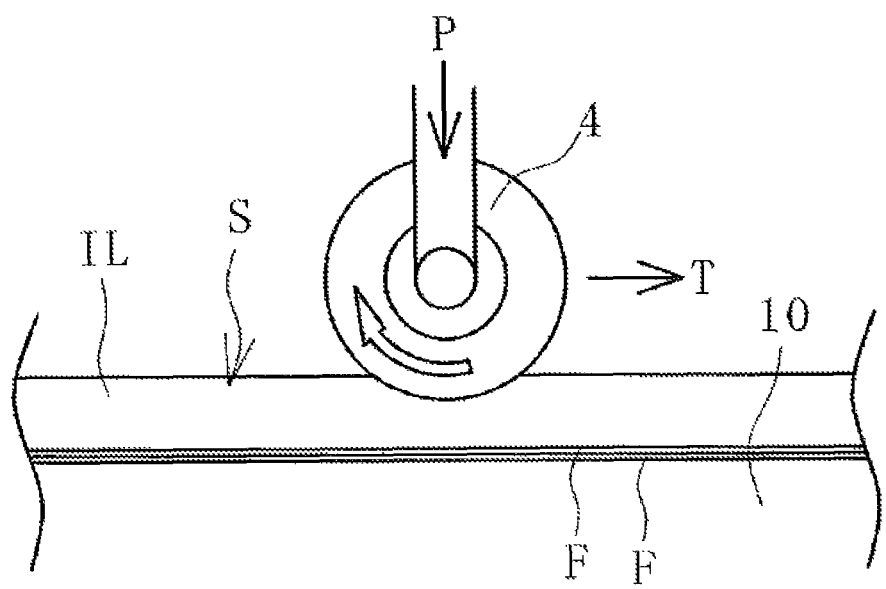
FIG. 4 is an enlarged view illustrating the periphery of the support roller in a case where two low-friction sheets are interposed between a lower surface of an evaluation subject and an upper surface of a substrate in FIG. 1.

Therefore, as illustrated in FIG. 4, it is also possible to interpose two (or a plurality) of low-friction sheets F between the lower surface of the evaluation subject S and the upper surface of the substrate 10. Due to this, it is possible to minimize the adverse influence with respect to the measurement accuracy caused by friction between the evaluation subject S and the substrate 10. It is possible to use fluorocarbon resin sheets or the like as the low-friction sheets F.

In the same manner as described above, low-friction sheets F (a low-friction material) may be used on the surfaces of the moving guides 11 which oppose the moving rollers 5 in order to suppress the adverse influence due to the friction between the moving rollers 5 and the moving guides 11.

Strictly speaking, the detected data (the tensile force T) of the tensile force sensor 6 includes not only the resistance to moving over the support roller 4, but also various resistances such as the rolling resistance of the moving rollers 5 and the rotation resistance of the holding roller 9. Therefore, in order to ascertain the resistance to moving over the support roller 4 with even higher accuracy, the support roller 4 is moved upward and set to a state of non-contact with the evaluation subject S and a base tensile force T1 is ascertained when the frame 2 is pulled by the wire 7 in this state. A tensile force Tr where the base tensile force T1 is subtracted from the tensile force T measured as described above may be evaluated as the resistance to moving over the support roller.

Figure 5:
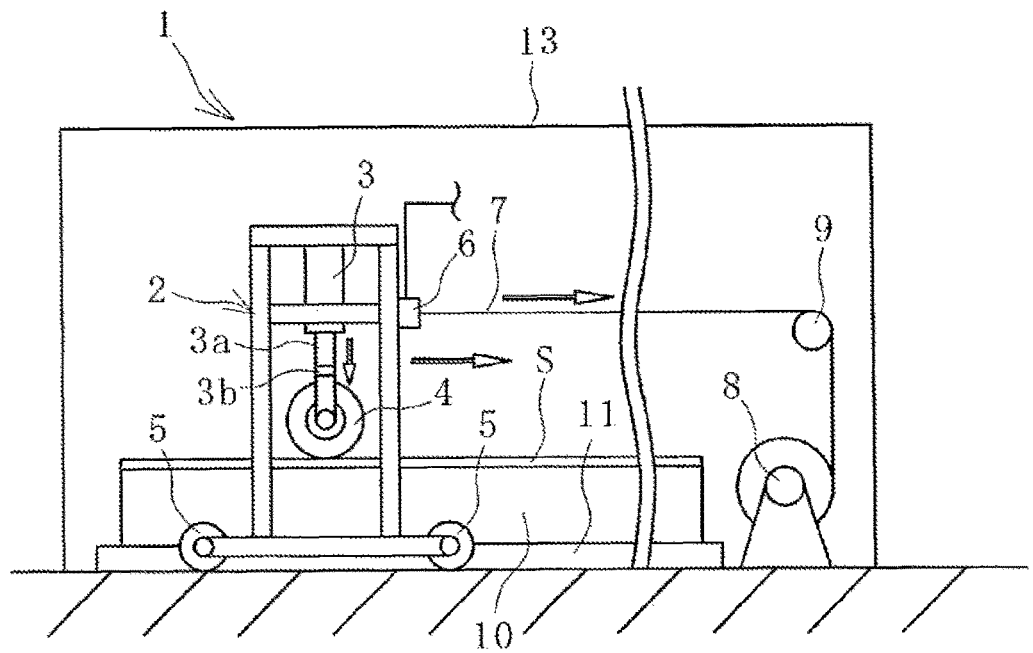
FIG. 5 is an explanatory drawing illustrating, as seen in side view, the device for measuring resistance to moving over a support roller of the present technology provided with a thermostatic chamber.

In addition, since the resistance to moving over the support roller is dependent on the temperature, it is possible for the measuring device 1 to be provided with a thermostatic chamber 13 as illustrated in FIG. 5 in order to be able to make the measurement under set temperature conditions (for example, −40° C. to 40° C. corresponding to areas with a cold climate and to areas with a hot climate). When the measurement of the tensile force T is performed by controlling the inside of the thermostatic chamber 13 to be a desired constant temperature, it is also possible to ascertain the temperature dependence of the resistance to moving over the support roller with higher accuracy. Here, it is not necessary to install the entirety of the measuring device inside the thermostatic chamber 13. The winding machine 8, the holding roller 9, the measuring apparatus 12, and the like may be arranged outside of the thermostatic chamber 13.

EXAMPLES

[Moving Over Resistance]

Figure 7:
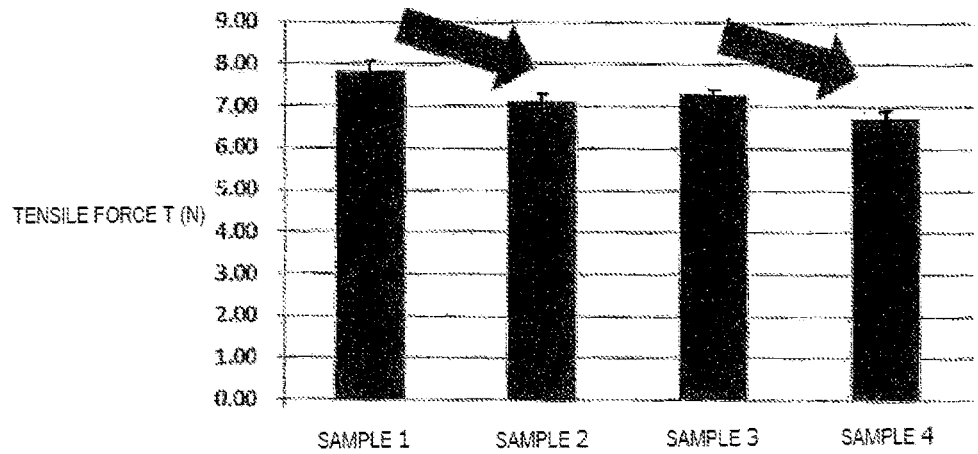
FIG. 7 is a graph showing resistances to moving over a support roller measured according to the present technology.

The tensile force T (the resistance to moving over the support roller) was measured for four types of evaluation subjects (samples 1 to 4) described in Table 1 using a measuring device with the same structure as the measuring device 1 illustrated in FIGS. 1 to 3 and the results of the measurement are shown in FIG. 7. Each of the samples had a size where the length was 4000 mm, the width was 150 mm, and the thickness was 9 mm. An external force of 31 N was applied vertically downward with respect to a support roller with a movement velocity of 0.92 m/s and a roller outer diameter of 90 mm.

TABLE 1

| | MATERIAL | TYPE |
|---|---|---|
| SAMPLE 1 | HIGH-DAMPING RUBBER (HRB) | GENERAL TYPE |
| SAMPLE 2 | HIGH-DAMPING RUBBER (HRB) | ENERGY-SAVING TYPE |
| SAMPLE 3 | STYRENE-BUTADIENE RUBBER (SBR) | GENERAL TYPE |
| SAMPLE 4 | STYRENE-BUTADIENE RUBBER (SBR) | ENERGY-SAVING TYPE |

It is understood from the results shown in FIG. 7 that the energy-saving type samples 2 and 4 each had a lower moving over resistance than the general type samples 1 and 3. Taking into account the relative magnitude of the moving over resistance, these results are substantially the same as a case where the resistance to moving over the support roller was measured using the actual conveyor belt, and thus it is understood that it is possible to measure the moving over resistance with high accuracy.

[Velocity Dependence of Moving Over Resistance]

Figure 8:
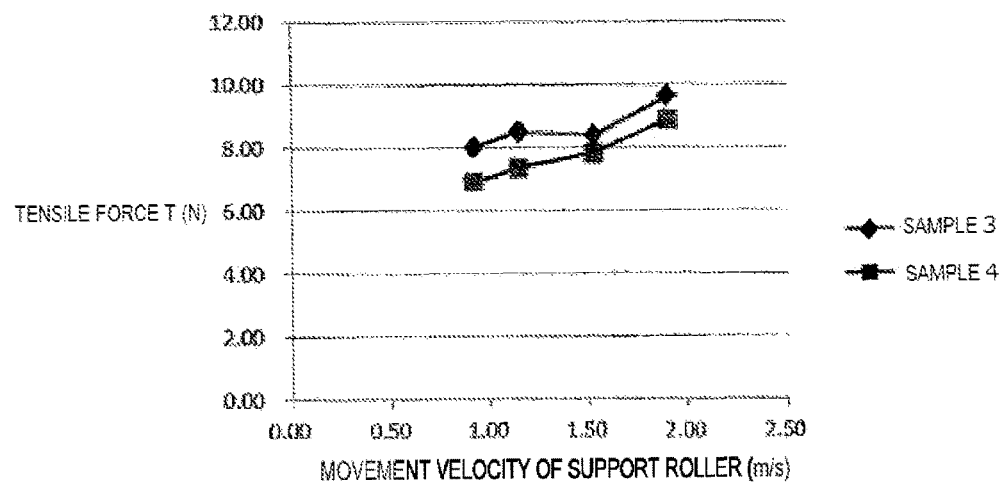
FIG. 8 is a graph showing velocity dependence of resistance to moving over a support roller measured according to the present technology.

Tensile forces T (the resistance to moving over the support roller) were measured using the measuring device 1 described above by differentiating the movement velocity of the support roller into four levels of 0.92 m/s, 1.15 m/s, 1.53 m/s, and 1.91 m/s for two types of evaluation subjects (samples 3 and 4) described in Table 1 and the results of the measurement are shown in FIG. 8. An external force of 31 N was applied vertically downward with respect to the support roller.

It is understood from the results shown in FIG. 8 that when the movement velocity of the support roller (that is, the belt velocity) increases, the tensile force T (the resistance to moving over the support roller) also increases. This result was the same as a case where the resistance to moving over the support roller was measured using the actual conveyor belt and it is understood that it is possible to ascertain the velocity dependence of the moving over resistance with high accuracy.

[Pressure Dependence of Moving Over Resistance]

Figure 9:
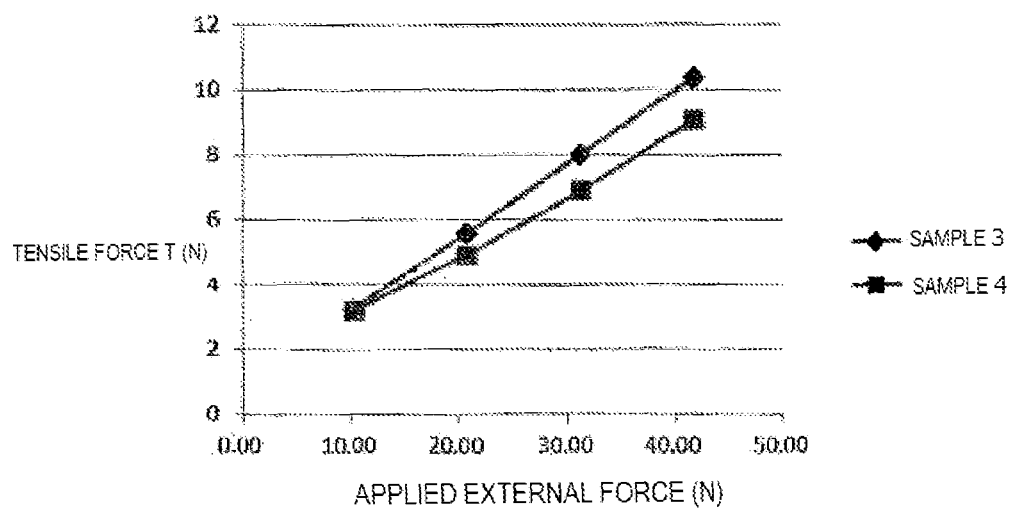
FIG. 9 is a graph showing pressure dependence of resistance to moving over a support roller measured according to the present technology.

Tensile forces T (the resistance to moving over the support roller) were measured using the measuring device 1 described above by differentiating the external force which was applied vertically downward to the support roller into four levels of 10.25 N, 20.75 N, 31.25 N, and 41.75 N for two types of evaluation subjects (samples 3 and 4) described in Table 1 and the results of the measurement are shown in FIG. 9. The movement velocity of the support roller was 0.92 m/s.

It is understood from the results shown in FIG. 9 that when the external force (the pressure) applied to the support roller increases, the tensile force T (the resistance to moving over the support roller) also increases. This result was the same as a case where the resistance to moving over the support roller was measured using an actual conveyor belt and it is understood that it is possible to ascertain the pressure dependence of the moving over resistance with high accuracy.

What is claimed is:

1. A method for measuring resistance of a conveyor belt to moving over a support roller, the support roller being rolled in a longitudinal direction of an evaluation subject formed by a cut sample of the conveyor belt in a state where the support roller is pressed at a predetermined pressure against a surface of the evaluation subject, the method comprising the steps of:
   mounting the evaluation subject on a flat substrate;
   horizontally pulling and rolling the support roller in the longitudinal direction of the evaluation subject in a state where the support roller is pressed vertically downward at a preset pressure against an upper surface of the evaluation subject without substantial deformation of an outer peripheral surface of the support roller; and
   evaluating tensile force in a horizontal direction measured at that time as resistance to moving over the support roller.

2. The method for measuring resistance of a conveyor belt to moving over a support roller according to claim 1, wherein the evaluation subject is a cut sample of only an inner periphery-side cover rubber layer.

3. The method for measuring resistance of a conveyor belt to moving over a support roller according to claim 2, wherein the support roller is set to a state of being pressed vertically downward at the preset pressure against the upper surface of the evaluation subject using a pneumatic cylinder.

4. The method for measuring resistance of a conveyor belt to moving over a support roller according to claim 3, wherein the support roller is horizontally pulled and moved in the longitudinal direction of the evaluation subject in a state of non-contact with the evaluation subject,
   tensile force in the horizontal direction measured at that time is set as a base tensile force,
   the support roller is set to a state of being pressed at the preset pressure against the upper surface of the evaluation subject, and
   tensile force obtained by subtracting the base tensile force from the tensile force in the horizontal direction measured when the support roller is horizontally pulled and rolled in the longitudinal direction of the evaluation subject is evaluated as the resistance to moving over the support roller.

5. The method for measuring resistance of a conveyor belt to moving over a support roller according to claim 4, wherein a plurality of low-friction sheets is interposed between a lower surface of the evaluation subject and an upper surface of the substrate.

6. The method for measuring resistance of a conveyor belt to moving over a support roller according to claim 1, wherein the support roller is horizontally pulled and moved in the longitudinal direction of the evaluation subject in a state of non-contact with the evaluation subject,
   tensile force in the horizontal direction measured at that time is set as a base tensile force,
   the support roller is set to a state of being pressed at the preset pressure against the upper surface of the evaluation subject, and
   tensile force obtained by subtracting the base tensile force from the tensile force in the horizontal direction measured when the support roller is horizontally pulled and rolled in the longitudinal direction of the evaluation subject is evaluated as the resistance to moving over a support roller.

7. The method for measuring resistance of a conveyor belt to moving over a support roller according to claim 1, wherein a plurality of low-friction sheets is interposed between a lower surface of the evaluation subject and an upper surface of the substrate.

8. A device for measuring resistance of a conveyor belt to moving over a support roller, the device having a support roller to be pressed at a predetermined pressure against a surface of an evaluation subject formed by a cut sample of a conveyor belt, and rolling means for rolling the support roller in a longitudinal direction of the evaluation subject in the pressed state, the device comprising:

a flat substrate for mounting the evaluation subject thereon;

pressing means for setting the support roller to a state of being pressed vertically downward at a preset pressure against an upper surface of the evaluation subject mounted on the substrate;

rolling means for horizontally pulling and rolling the support roller set to the pressed state in the longitudinal direction of the evaluation subject; and a tensile force sensor for measuring tensile force in a horizontal direction during the rolling, the support roller being configured so that an outer peripheral surface thereof is substantially not deformed in the pressed state.

9. The device for measuring resistance of a conveyor belt to moving over a support roller according to claim 8, wherein a cut sample of only an inner periphery-side cover rubber layer is used as the evaluation subject.

10. The device for measuring resistance of a conveyor belt to moving over a support roller according to claim 9, wherein a pneumatic cylinder is used as the pressing means.

11. The method for measuring resistance of a conveyor belt to moving over a support roller according to claim 1, wherein the support roller is set to a state of being pressed vertically downward at the preset pressure against the upper surface of the evaluation subject using a pneumatic cylinder.

12. The device for measuring resistance of a conveyor belt to moving over a support roller according to claim 8, wherein a pneumatic cylinder is used as the pressing means.

* * * * *